(12) United States Patent
Sarks et al.

(10) Patent No.: US 11,098,327 B2
(45) Date of Patent: Aug. 24, 2021

(54) METHODS AND SYSTEMS FOR STARCH BASED PROPAGATION OF A MICROORGANISM

(71) Applicant: POET Research, Inc., Sioux Falls, SD (US)

(72) Inventors: Cory James Sarks, Sioux Falls, SD (US); Malgorzata M. Slupska, Sioux Falls, SD (US); David Charles Carlson, Brandon, SD (US); Benjamin M. Gerdes, Yankton, SD (US); Neelakantam V. Narendranath, Fort Mill, SC (US); David D. Bushong, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 103 days.

(21) Appl. No.: 16/310,173

(22) PCT Filed: Jun. 12, 2017

(86) PCT No.: PCT/US2017/036958
§ 371 (c)(1),
(2) Date: Dec. 14, 2018

(87) PCT Pub. No.: WO2017/218380
PCT Pub. Date: Dec. 21, 2017

(65) Prior Publication Data
US 2019/0256873 A1    Aug. 22, 2019

Related U.S. Application Data

(60) Provisional application No. 62/351,036, filed on Jun. 16, 2016.

(51) Int. Cl.
*C12N 1/18*   (2006.01)
*C12P 7/06*   (2006.01)
*C12M 1/00*   (2006.01)
*C12N 9/26*   (2006.01)

(52) U.S. Cl.
CPC ............... *C12P 7/06* (2013.01); *C12M 21/12* (2013.01); *C12N 1/18* (2013.01); *C12N 9/2414* (2013.01); *C12Y 302/01001* (2013.01); *C12Y 302/01003* (2013.01); *Y02E 50/10* (2013.01)

(58) Field of Classification Search
CPC ........ C12M 21/12; C12N 1/18; C12N 9/2414; C12Y 302/01001; C12Y 302/01003; C12Y 302/01; C12P 7/06; Y02E 50/10
See application file for complete search history.

(56) References Cited

FOREIGN PATENT DOCUMENTS

| WO | 2014159529 A1 | 10/2014 |
| WO | 2014160184 A1 | 10/2014 |
| WO | 2016205596 A1 | 12/2016 |

OTHER PUBLICATIONS

Parreiras et al., PLOS ONE, Sep. 2014, vol. 9, Issue 9, e107499, p. 1-17.*
Szymanowska-Powalowska et al., Fuel, 2014, vol. 119, p. 328-334.*
Li et al., "Bacterial community structure and dynamics during corn-based bioethanol fermentation", Microbial Ecology, vol. 71, pp. 409-421 Sep. 17, 2015, (13 pages).
Tomas-Pejo et al., "Influence of the propagation strategy for obtaining robust *Saccharomyces cervevisiae* cells that efficiently co-ferment xylose and glucose in lignoceliulosic hydrolysates", Microbial Biotechnology, vol. 8, pp. 999-1005, 2015, (8 pages).
International Search Report for International Application No. PCT/US2017/036958, dated Oct. 8, 2017 (3 pages).

* cited by examiner

*Primary Examiner* — Kade Ariani
(74) *Attorney, Agent, or Firm* — Kagan Binder, PLLC (57) ABSTRACT

Systems and methods that include starch derived from grain as a carbon source for propagation of microorganisms.

20 Claims, 9 Drawing Sheets

METHODS AND SYSTEMS FOR STARCH BASED PROPAGATION OF A MICROORGANISM

RELATED APPLICATIONS

The present application claims the benefit of commonly owned provisional application having Ser. No. 62/351,036, filed on Jun. 16, 2016, which provisional application is incorporated herein by reference in its entirety.

FIELD

The present invention relates to using starch based propagation media to reproduce microorganisms such as yeast cells used in cellulosic ethanol production.

SUMMARY

In some embodiments of the present disclosure is a method of propagating a microorganism, the method comprising:

a) providing a carbon source, wherein the carbon source comprises a ground grain slurry, wherein the ground grain slurry comprises starch;

b) providing a nutrient source, wherein the nutrient source comprises a grain stillage composition;

c) providing a source of a first cell mass of a microorganism that can covert a monosaccharide into a biochemical;

d) providing a source of one or more enzymes than can convert the starch into one or more monosaccharides;

e) combining the carbon source, the nutrient source, the first cell mass of the microorganism, and the one or more enzymes to form a propagation composition, wherein the propagation composition is exposed to conditions to convert the starch into glucose and propagate the first cell mass of the microorganism into a second cell mass of the microorganism.

In some embodiments of the present disclosure is a system for propagating a microorganism, the system comprising:

a) a carbon source comprising a ground grain slurry, wherein the ground grain slurry comprises starch;

b) a nutrient source, wherein the nutrient source comprises a grain stillage composition;

c) a source of a first cell mass of a microorganism that can covert a monosaccharide into a biochemical;

d) a source of one or more enzymes than can convert the starch into one or more monosaccharides;

e) at least one vessel in fluid communication with the carbon source, the nutrient source, the first cell mass of the microorganism, and the one or more enzymes, wherein the at least one vessel is configured to combine the carbon source, the nutrient source, the first cell mass of the microorganism, and the one or more enzymes to form a propagation composition, where in the vessel is configured to expose the propagation composition to conditions to convert the starch into glucose and propagate the first cell mass of the microorganism into a second cell mass of the microorganism.

DETAILED DESCRIPTION

Disclosed in embodiments herein are methods and systems for using grain starch (e.g., corn grain starch) to propagate a "seed" microorganism into a larger population of microorganisms. Propagating a "seed" microorganism can also be referred to as "seed fermentation." After propagation ("seed fermentation"), the larger population of microorganisms can be added into cellulosic hydrolysate (e.g., hydrolysate derived from corn cobs and corn stover) so as to convert one or more monosaccharides into one or more biochemicals. Advantageously, methods and systems according to the present disclosure can help create better and healthier yeast during propagation that can then be used in cellulosic ethanol systems.

Figure 1:
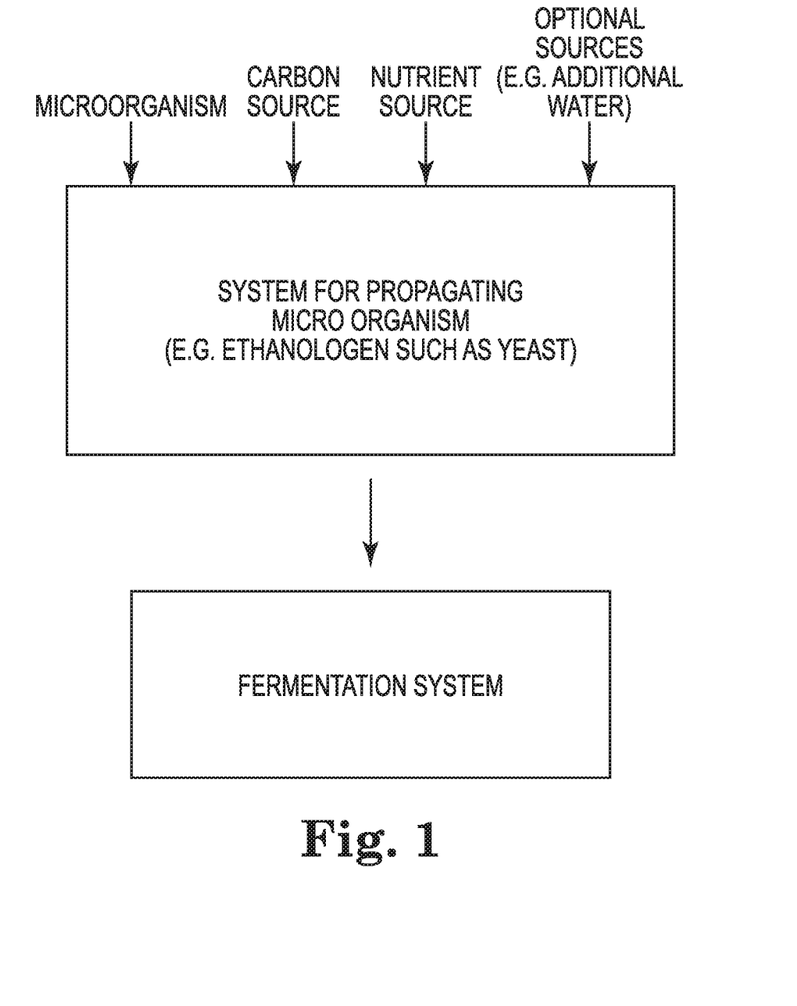
FIG. 1 shows a process flow diagram for propagating a microorganism that can be used in a fermentation system to convert one or more monosaccharides into one or more biochemicals.

As shown in FIG. 1, a system for propagating a microorganism can include combining at least a carbon source, a nutrient source, and a first cell mass of a microorganism under conditions to reproduce in number and form a second cell mass that is greater in cell number as compared to the first cell mass. Optionally, one or more additional components can be added to the propagation system such as water and the like.

Microorganisms

Microorganisms that can convert one or more monosaccharides into a biochemical include, e.g., bacteria and/or fungi such as yeast. The product biochemicals can vary depending on the conditions that are provided. In many embodiments, the biochemicals include biofuels such as ethanol, butanol, and the like. In some embodiments, the microorganism includes one or more ethanologenic microorganisms referred to as "ethanologens". As used herein, an "ethanologen" refers to a microorganism that can convert one or more monosaccharides (e.g., glucose and the like) into at least ethanol.

Exemplary yeast and fungus include the genus of, *Aspergillus, Candida, Pichia*, (*Hansenula*), *Phanerochaete, Kloeckera* (*Hanseniaspora*), *Kluyveromyces, Rhodotorula, Torulopsis, Zygosaccharomyces, Yarrowia*, and *Saccharomyces*. In some embodiments, the yeast is a strain of *Saccharomyces cerevisiae* yeast. In some embodiments, the microorganism to be propagated includes genetically modified yeast such as genetically modified *Saccharomyces cerevisiae* that can convert glucose and xylose into a biochemical such as ethanol.

Nutrient Source

A nutrient source is also included to help propagate microorganisms such as ethanologens. As used herein, a "nutrient source" refers to one or more materials that can be used by a microorganism to grow and/or reproduce to create additional microorganisms and is different from a carbon source or can be used as a carbon source as well.

In some embodiments, the nutrient source used includes a stillage composition (e.g. whole stillage, thin stillage and/or syrup). Whole stillage is a byproduct of distilling a fermentation product. For example, a process for making whole stillage is a corn grain-to-ethanol process. For example, a grain such as corn, barley, wheat, and/or sorghum can be fermented into a fermentation product that includes one or more biochemicals such as ethanol. Either the ground whole grain can be used or only one or more portions of the grain can be used. For example, whole grains can be dry milled for fermentation or fractionated into one or more separated portions before milling. After milling, the milled grain material can be further processed to break down polysaccharides and/or oligosaccharides into one or more monosaccharides such as glucose that can be fermented by, e.g., yeast. Methods of breaking down polysaccharides such as starch into glucose include e.g. hot water, such as hot water that includes an added acid such as sulfuric acid, and/or enzymatic pretreatment. After fermentation, the fermentation product is distilled in a system where the ethanol is removed from the fermented mash in a distillation column. After the ethanol is removed, the remaining residue is removed as stillage residue. The stillage residue is known as "whole stillage." The whole stillage can be optionally further processed via one or more systems to further clarify or separate the whole stillage before being delivered to a propagation system such as in FIG. 1. For example, the whole stillage can be subjected to a solid-liquid separation process to produce a solid stream of residue, also known as wet cake, and a liquid stream of residue, also referred to as thin stillage. The thin stillage can be further processed to increase the solids concentration by evaporation resulting in condensed distillers solubles or syrup.

Such stillage composition from the grain-to-ethanol producing process, including the whole stillage, wet cake, thin stillage, and/or syrup can be used as at least part of the nutrient source for propagating microorganisms such as yeast. Using at least a portion of the whole stillage provides an alternative or additional nutrient source as compared to, e.g., yeast extract. Using whole stillage (e.g. thin stillage) as the entire amount of nutrients or part of the nutrients can propagate yeast as well as, or better than, other nutrient sources such as yeast extract.

In some embodiments, the nutrient source includes a stillage composition such as thin stillage, wetcake, syrup, and any combination thereof. The nutrient source can include syrup derived from thin stillage, thin stillage, or combinations thereof.

The stillage composition can be provided in any amount so as to help reproduce (propagate) and generate a desired population of microorganism (e.g., ethanologen) within a given amount of time. The amount of stillage component provided can depend on factors such as the type and amount of other nutrient sources present, the type and amount of carbon sources present, pH, temperature, desired time period for propagation, and the like. In some embodiments, the nutrient source includes only thin stillage.

In some embodiments, the thin stillage can be provided to the propagation system at a temperature in the range from 70 to 95° C., or even from 80 to 90° C.

Carbon Source

As used herein, a "carbon source" refers to one or more compounds that include at least one carbon atom and can be used by a microorganism such as yeast to grow and/or reproduce to create additional biomass. Exemplary carbon sources include monosaccharides such as glucose, fructose, galactose, mannose, xylose and the like; disaccharides such as lactose, maltose, sucrose, cellobiose and the like; oligosaccharides; polysaccharides such as cellulose, hemicelluloses, starch, xylane and the like; single carbon substrates including only one carbon atom such as methanol; and polyols such as glycerol, but not limited thereto.

In a cellulosic process that uses biomass such as corn cobs and/or corn stover, the carbon source can include a hydrolysate from acid hydrolysis, steam explosion, enzymatic liquefaction, and/or enzymatic saccharification. Unfortunately such sources of a carbon source can include components that are toxic (toxins) to microorganisms such as yeast. Such toxins include furfural, hydroxymethylfurfural, acetic acid, and the like. Using yeast and furfural as an example for illustration purposes, yeast tend to degrade at least a portion of furfural before performing other metabolic activity such as propagation and/or fermentation. Thus, especially in a large scale commercial operation, yeast may spend an undue amount of time (e.g., 24 hours) degrading furfural before propagating yeast into additional yeast cells. This can make propagation economically undesirable and/or put a strain on the yeast and may cause a less healthy yeast population to be produced. Further, bacterial contamination (e.g., lactic acid bacteria) is often present in propagation, fermentation, and the like. Such bacteria can compete with the yeast for sugar and can have a "head start" relative to the yeast in consuming sugar while the yeast is degrading furfural. Such a competition for sugar can be an additional strain on the yeast and may cause a less healthy yeast population to be produced.

Accordingly, there is a continuing desire to identify a propagation media substantially free of furfural for yeast propagation and/or to better out-compete bacterial contamination, especially in the context of cellulosic fermentation process. Also desired are methods and system to generate better quality ("healthier") and/or greater yeast quantity to more quickly detoxify (degrade) furfural that is eventually encountered by the yeast during fermentation of a cellulosic hydrolysate (e.g., corn stover and corn cob hydrolysate) to speed up fermentation, improve fermentation, and/or out-compete bacterial contamination.

An alternative propagation media has been discovered where at least the cellulosic saccharification broth used as carbon source in the propagation composition (medium) is replaced at least in part by starch ethanol plant corn slurry. Starch ethanol plant corn slurry is substantially free of furfural. Traditional alpha-amylases and gluco-amylases that are commercially available may be used hydrolyse the starch to form the glucose for propagation.

Embodiments of the present disclosure include a carbon source such as starch derived from a grain such as corn. The starch can be hydrolyzed into glucose prior to being combined with yeast for propagation or in-situ as the yeast is being propagated. Further, at least a portion of the starch can be hydrolyzed prior to adding yeast while the remainder of the starch is hydrolyzed in the presence of yeast. Hydrolyzing grain starch such as corn starch can be performed in a manner that avoids generation of toxins such as furfural. Advantageously, the yeast can avoid having to degrade furfural, thereby avoiding lag time associated with degrading the furfural. Thus, the head start on sugar consumption by bacteria (discussed above) can be reduced or avoided completely. In addition, while not being bound by theory, it is believed that the yeast are not unduly stressed during propagation due to having to degrade furfural and, thus, a relatively healthier, more robust, yeast population is created that can better withstand eventual exposure to toxins such as furfural that may be present in hydrolysate compositions such as those derived from corn stover and corn cobs.

Propagation

Figure 2:
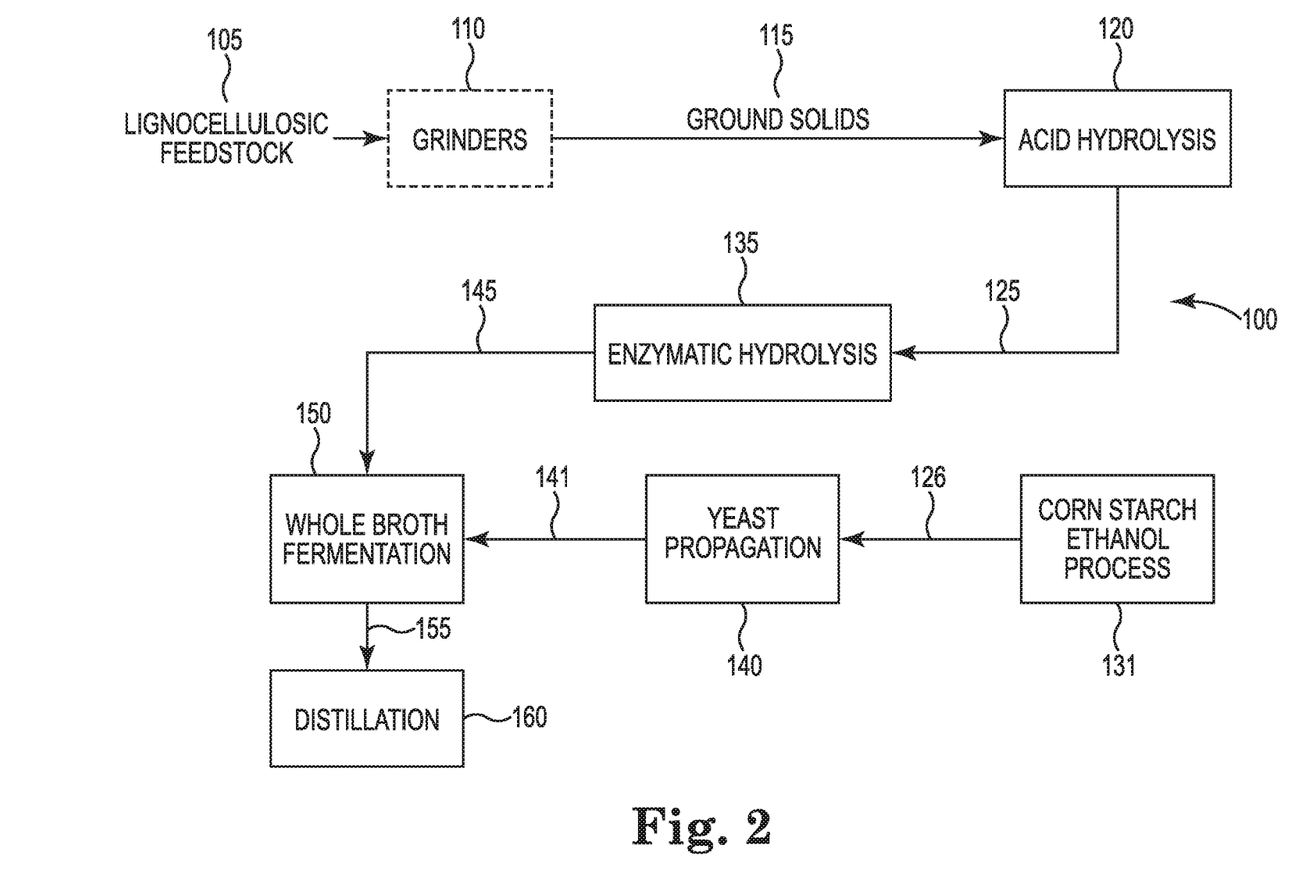
FIG. 2 shows a process flow diagram of an embodiment according to the present disclosure.
Figure 3A:
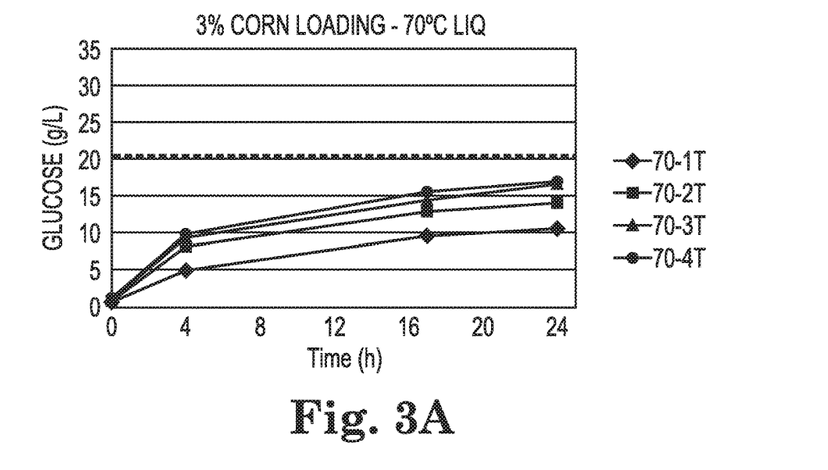
FIG. 3A shows a graph for data in Example 1.
Figure 3B:
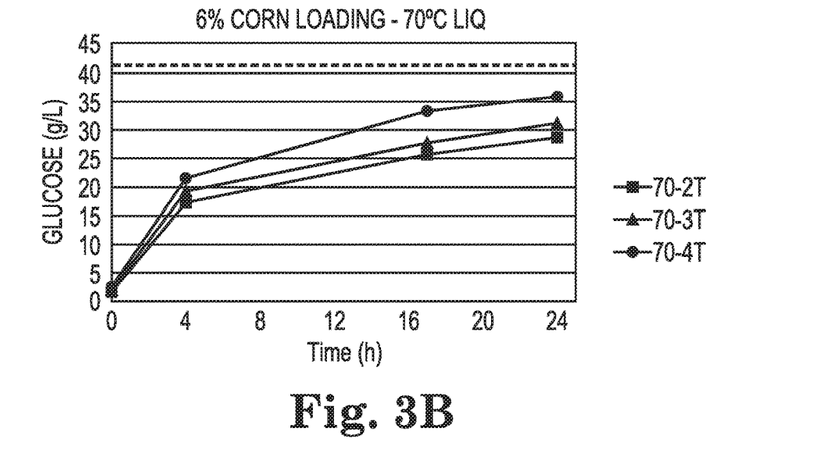
FIG. 3B shows another graph for data in Example 1.
Figure 3C:
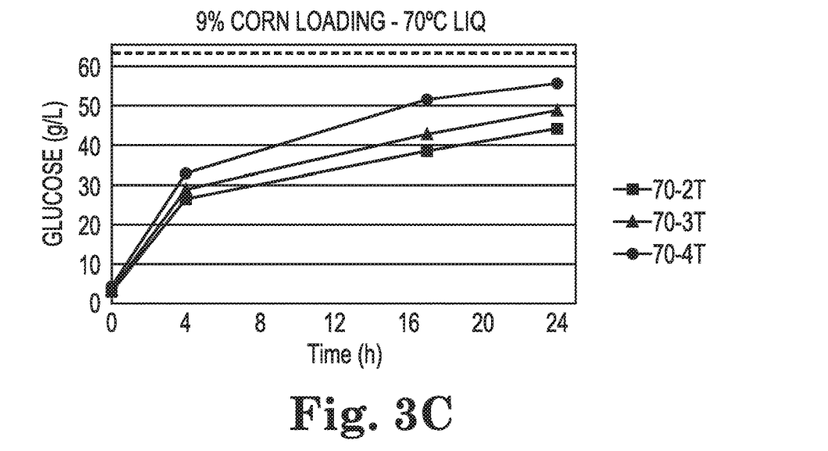
FIG. 3C shows another graph for data in Example 1.
Figure 4A:
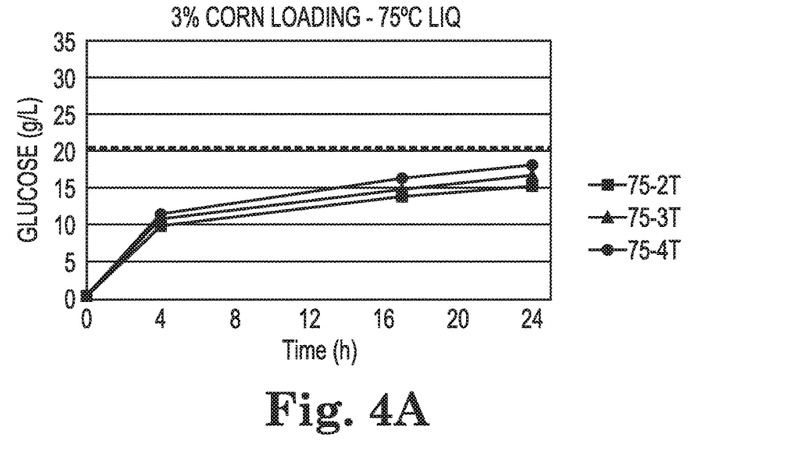
FIG. 4A shows another graph for data in Example 1.
Figure 4B:
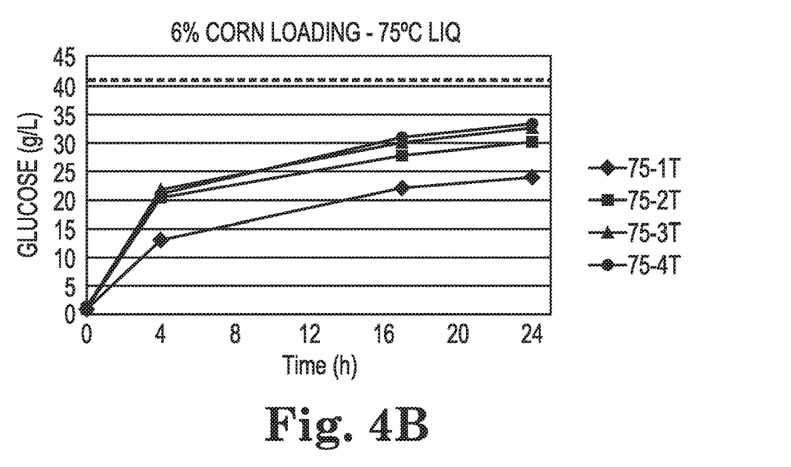
FIG. 4B shows another graph for data in Example 1.
Figure 4C:
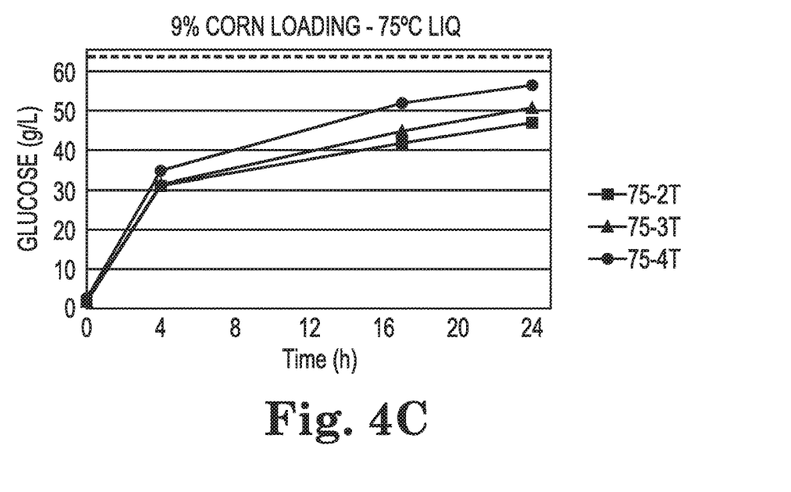
FIG. 4C shows another graph for data in Example 1.
Figure 5A:
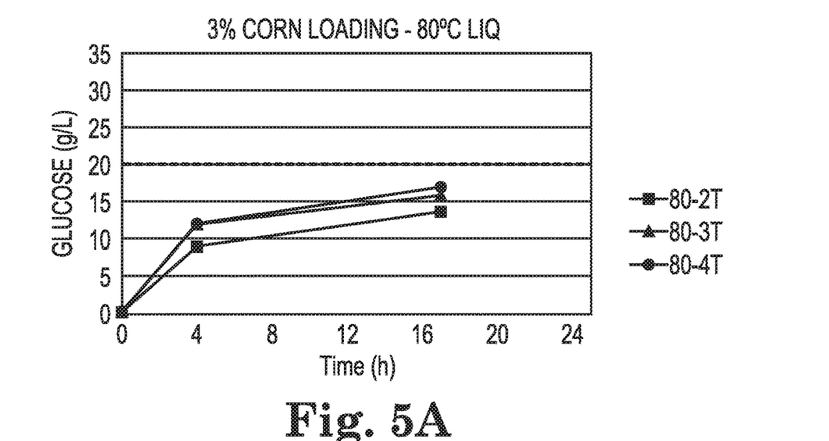
FIG. 5A shows another graph for data in Example 1.
Figure 5B:
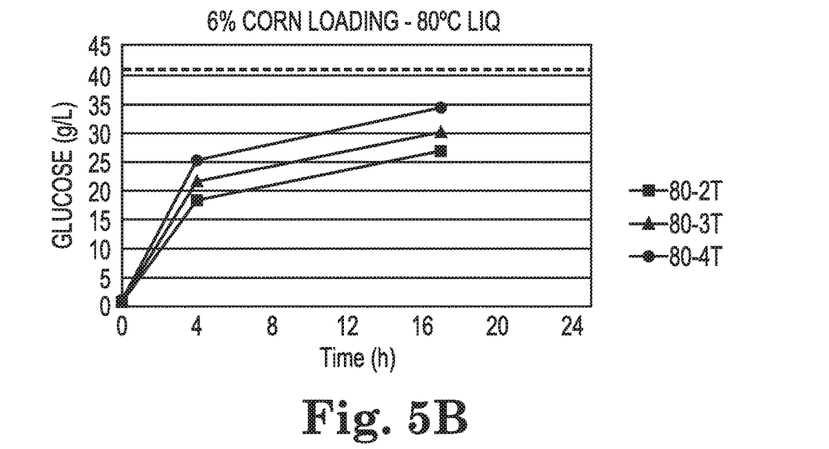
FIG. 5B shows another graph for data in Example 1.
Figure 5C:
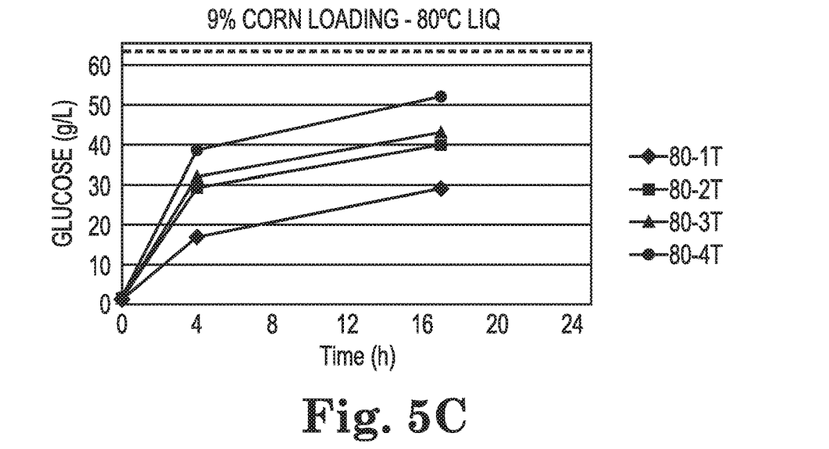
FIG. 5C shows another graph for data in Example 1.

FIG. 2 illustrates an embodiment according to the present disclosure. FIG. 2 represents a biorefinery having a corn-grain ethanol process co-located with a cellulosic ethanol process. Such processes can be physically located relatively near each other such as within several hundred yards such that piping and like can be easily installed between the two processes. As shown in FIG. 2, ground grain slurry 126 is provided to a propagation system 140 from a corn starch ethanol process 131. The ground grain slurry can include ground corn grain slurry that includes corn starch. In some embodiments, the ground corn grain is formed by dry grinding whole corn grain in corn ethanol process 131. In some embodiments, the whole ground corn grain can be combined with water and thin stillage to form a pumpable slurry that can be pumped to propagation system 140. In some embodiments, one or more pipe lines used to pump the corn slurry can be flushed with water such as distillate from corn ethanol process 131. Such water can be used to make a propagation composition in the propagation system 140. Propagation system 140 can include at least one vessel in fluid communication with the ground grain slurry 126 so that the grain slurry can be added to the at least one vessel. In some embodiments, ground grain slurry 126, a nutrient source (e.g. thin stillage), a first cell mass of a microorganism (e.g., yeast), and at least one alpha-amylase can be added to the at least one vessel of the propagation system 140 and held at a temperature in the range from 65° C. to 80° C. (e.g., about 70° C.) for a time period in the range from 1 to 3 hours. During this time period, the alpha-amylase can facilitate converting at least a portion of the starch to one or more oligosaccharides. Also, this temperature holding period can help pasteurize at least a portion of any bacterial contamination that may be present. Advantageously, including pasteurization and avoiding furfural in this manner can help the yeast propagate sooner and with less competition for glucose.

In some embodiments, the contents of the at least one vessel can be cooled to a temperature in the range from 20° C. to 40° C. (e.g., about 31° C.). During and/or after cooling, gluco-amylase can be added to facilitate converting one or more oligosaccharides into glucose so that the first cell mass of the microorganism can utilize the glucose to propagate into the second cell mass of the microorganism. In some embodiments, a propagation vessel can be coupled to an aerator to facilitate propagation. A propagation composition can be held at a temperature in the range from 20° C. to 40° C. (e.g., about 31° C.) for a time period of from 10-20 hours (e.g., about 15-16 hours).

In some embodiments, the second cell mass of the microorganism is at least 500 times greater in number than the first cell mass of the microorganism, at least 1000 times greater in number than the first cell mass of the microorganism, at least 1500 times greater in number than the first cell mass of the microorganism, at least 2000 times greater in number than the first cell mass of the microorganism, or even at least 3000 times greater in number than the first cell mass of the microorganism.

In some embodiments, the first cell mass of the microorganism is $5 \times 10^{\wedge}6$ cells per milliliter of propagation composition or less, $1 \times 10^{\wedge}6$ cells per milliliter of propagation composition or less, $5 \times 10^{\wedge}5$ cells per milliliter of propagation composition or less, or even $1 \times 10^{\wedge}5$ cells per milliliter of propagation composition or less.

In some embodiments, the second cell mass of the microorganism is $1 \times 10^{\wedge}7$ cells per milliliter of propagation composition or more, $5 \times 10^{\wedge}7$ cells per milliliter of propagation composition or more, $1 \times 10^{\wedge}8$ cells per milliliter of propagation composition or more, $5 \times 10^{\wedge}8$ cells per milliliter of propagation composition or more, or even $1 \times 10^{\wedge}9$ cells per milliliter of propagation composition or more.

Optionally, one or more additional components can be added to the at least one vessel to form a propagation composition. For example, process water from the cellulosic ethanol process and/or hot distillate from a corn ethanol process and/or cellulosic ethanol process can be added if more water is desired.

In some embodiments, a propagation composition in propagation system 140 can include between 5 to 25% by volume of ground corn slurry; between 20-30% by volume of thin stillage as a nutrient source; enzymes; yeast; and the balance water (e.g., cellulosic process water and/or corn ethanol distillate).

After propagation in propagation system 140, the propagation composition including the second cell mass of yeast 141 can be combined with a lignocellulosic hydrolysate in whole broth fermentation system 150 so that the second cell mass of organism can convert glucose and/or xylose into a biochemical in a continuous manner.

The remainder of the cellulosic ethanol system 100 in FIG. 2 is discussed below.

Before hydrolysis, a lignocellulosic feedstock can be prepared by a variety of techniques such as size reduction, steaming, combinations of these, and the like. As shown in FIG. 2, lignocellulosic feedstock 105 can be prepared prior to hydrolysis such as by grinding the lignocellulosic feedstock in one or more grinders 110 into ground solids 115 to reduce the size of the feedstock and increase its surface area for contact with a hydrolysis medium.

Acid Hydrolysis

FIG. 2 shows an embodiment of hydrolyzing lignocellulosic feedstock by passing a whole broth hydrolysate from acid hydrolysis 120 to enzymatic saccharification 135.

As shown in FIG. 2, acid hydrolysis 120 can convert hemicellulose in the ground biomass 115 into one or more pentoses such as xylose. In some embodiments, the acid hydrolysis includes contacting lignocellulosic biomass with an aqueous composition to hydrolyze at least a portion of the hemicellulose into one or more oligosaccharides and/or one or more pentoses, and form a first whole broth hydrolysate composition including at least pentose, cellulose, lignin, and furfural. In some embodiments, acid hydrolysis hydrolyzes at least a portion of cellulose into glucose.

During acid hydrolysis, the "severity" can be adjusted by varying one or more of time period, temperature, and pH of hydrolysis. In some embodiments, during hydrolysis an aqueous composition can have a pH in the range from 1 to 5, or even 2 to 3. The aqueous composition can include an acid such as sulfuric acid present in a concentration in the range from 0.2 to 1.3% w/w, or even 0.5 to 1% w/w. In some embodiments, acid hydrolysis can be performed for a time period in a range from 15 minutes to 5 hours, or even 30 minutes to 4 hours. In some embodiments, acid hydrolysis can be performed at a temperature in the range from greater than 100° C. to 170° C., or even from 110° C. to 150° C.

Acid hydrolysis can be performed in a variety of system and apparatus configurations. In some embodiments, an acid hydrolysis system can include a first reactor system in fluid communication with a source of lignocellulosic biomass and a source of an aqueous composition. The first reactor system can include at least one reactor configured to contact the lignocellulosic biomass with the aqueous composition to hydrolyze at least a portion of the hemicellulose into one or more oligosaccharides and/or one or more pentoses, and form a first, whole broth hydrolysate composition including at least pentose, cellulose, lignin, and furfural.

Optional Steam Explosion

Optionally, the whole broth hydrolysate 125 from acid hydrolysis 120 can be subjected to steam explosion conditions that make the cellulose in the whole broth hydrolysate 125 more accessible during enzymatic hydrolysis 135. In some embodiments, steam explosion also forms furfural. Steam explosion (not shown) can be performed in a system that includes at least one reactor configured to receive the hydrolysate composition and subject the cellulose in the hydrolysate composition to a steam explosion process under conditions that form a steam-exploded, hydrolysate composition including at least cellulose, lignin, and furfural.

During steam explosion, cellulose (either in a whole broth hydrolysate or hydrolysate with a portion of xylose liquor removed) can be subjected to a relatively elevated pressure and temperature so that moisture impregnated within the cellulose network is in a liquid state. Then, the pressure can be reduced so that the liquid "flashes" to a gas state so that the sudden expansion with the cellulose network causes at least a portion of the cellulose structure to rupture, thereby increasing the surface area of the cellulose for increased exposure to cellulase enzymes. In some embodiments, the superheated hydrolysate composition can be flashed to a reduced pressure by continuously discharging the composition through an orifice. In some embodiments, a hydrolysate composition including cellulose can be subjected to a temperature in the range from 320° F. to 400° F. and a pressure in the range from 75 psig to 235 psig, followed by suddenly exposing the hydrolysate composition to a reduced pressure such as atmospheric pressure. In some embodiments, a hydrolysate composition including cellulose can be subjected to a temperature in the range from 350° F. to 385° F. and a pressure in the range from 120 psig to 195 psig, followed by suddenly exposing the hydrolysate composition to a reduced pressure such as atmospheric pressure.

After steam explosion, the solid cellulose in the hydrolysate can be subjected to enzymatic hydrolysis 135.

Enzymatic Hydrolysis

As shown in FIG. 2, after acid hydrolysis 120 and optional steam explosion, at least a portion of the cellulose in the hydrolysate composition can be enzymatically hydrolyzed 135 to hydrolyze the cellulose in into glucose. In some embodiments, as shown in FIG. 2, at least a portion of the cellulose in the first whole broth hydrolysate composition 125 provided directly from acid hydrolysis 120 can be enzymatically hydrolyzed.

In some embodiments, enzymatic hydrolysis 135 can include liquefying (liquefaction) at least a portion of the cellulose in the hydrolysate 125 followed by saccharifying (saccharification) at least a portion of the liquefied cellulose to form glucose. Liquefaction can include adding one or more cellulase enzymes to the whole broth hydrolysate composition 125 to liquefy at least a portion of the cellulose.

A liquefaction system can include one or more vessels (not shown) containing a whole broth hydrolysate and configured to maintain the whole broth hydrolysate at a pH and temperature for a time period to convert at least a portion of the cellulose in the lignocellulosic biomass into an oligosaccharide and/or a monosaccharide. In some embodiments, the temperature of the whole broth hydrolysate during at least a portion of liquefaction is in a range from 45° C. to 65° C., or even from 50° C. to 60° C. In some embodiments, the pH of the whole broth hydrolysate during at least a portion of liquefaction is in a range from 4 to 6, or even from 4.5 to 5.5. In some embodiments, the liquefaction time period is in the range from 2 to 20 hours, or even from 6 to 8 hours.

A saccharification system can be in fluid communication with the liquefaction system. In some embodiments, a saccharification system can include at least one reactor configured to receive the liquefied cellulose so as to saccharify at least a portion of the liquefied cellulose and form glucose. A saccharification system can include one or more batch reactors (not shown) in fluid communication with the liquefaction system to receive the liquefied cellulose. The saccharification system can be configured to maintain a whole broth hydrolysate at a pH and a temperature for a time period to convert at least a portion of the cellulose in the lignocellulosic biomass into an oligosaccharide and/or a monosaccharide. In some embodiments, the temperature of the whole broth hydrolysate can be in a range from 45° C. to 65° C., or even from 50° C. to 60° C. In some embodiments, the pH of the whole broth hydrolysate can be in a range from 4 to 6, or even from 4.5 to 5.5. In some embodiments, the saccharification time period is in the range from 48 to 120 hours, or even from 112 to 114 hours.

After enzymatic hydrolysis in system 135, stream 145 can be fed into fermentation system 150 so that yeast from propagation system 140 can convert xylose and glucose into ethanol. The beer 155 from fermentation system 150 can be fed to distillation system 160 to recover a biochemical such as ethanol.

Example 1

Example 1 relates to the graphs in FIGS. 3A-5C, which show that alpha-amylase at different concentrations (1 T=0.007% w/w as-is corn, 2 T=0.013% w/w as-is corn, 3 T=0.025% w/w as-is corn, and 4 T=0.05% w/w as-is corn) is effective at generating glucose after cooling to 31.1° C. and adding gluco-amylase (1 T=0.012% w/w as-is corn, 2 T=0.025% w/w as-is corn, 3 T=0.035% w/w as-is corn, and 4 T=0.05% w/w as-is corn).

Pasteurization was performed at 70° C., 75° C., and 80° C. for two hours. This process was able to approach the theoretical maximum sugar release despite the enzymes not being at their optimal conditions. The flat, dashed line in each of FIGS. 3A-5C represents the theoretical maximum sugar concentration.

Example 2

Figure 6:
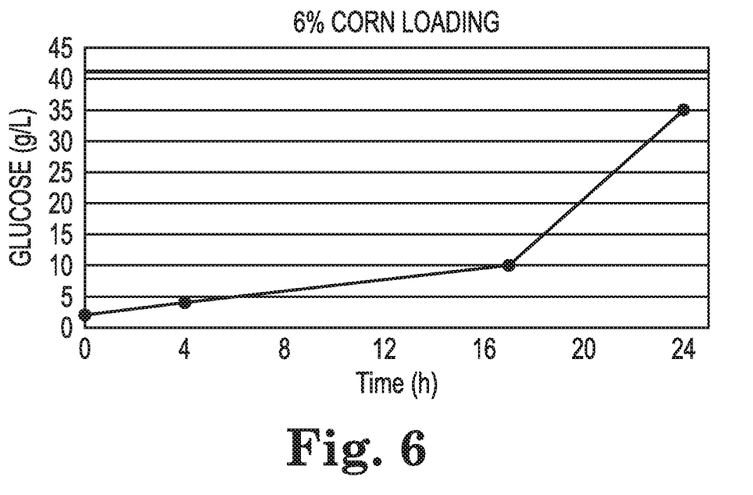
FIG. 6 shows a graph for data in Example 2.

Example 2 illustrates how incremental gluco-amylase may be added to a propagation media to create the exponential sugar release profile shown in FIG. 6. The benefit of the exponential sugar release compared to the logarithmic sugar release shown in Example 1 with alpha-amylase and gluco-amylase is limitation of sugar going to ethanol due to the Crabtree Effect. The Crabtree Effect is the production of ethanol and $CO_2$ during aerobic conditions due to high sugar concentrations. The production of ethanol would reduce the amount of sugar going to cell mass.

Example 3

Figure 7A:
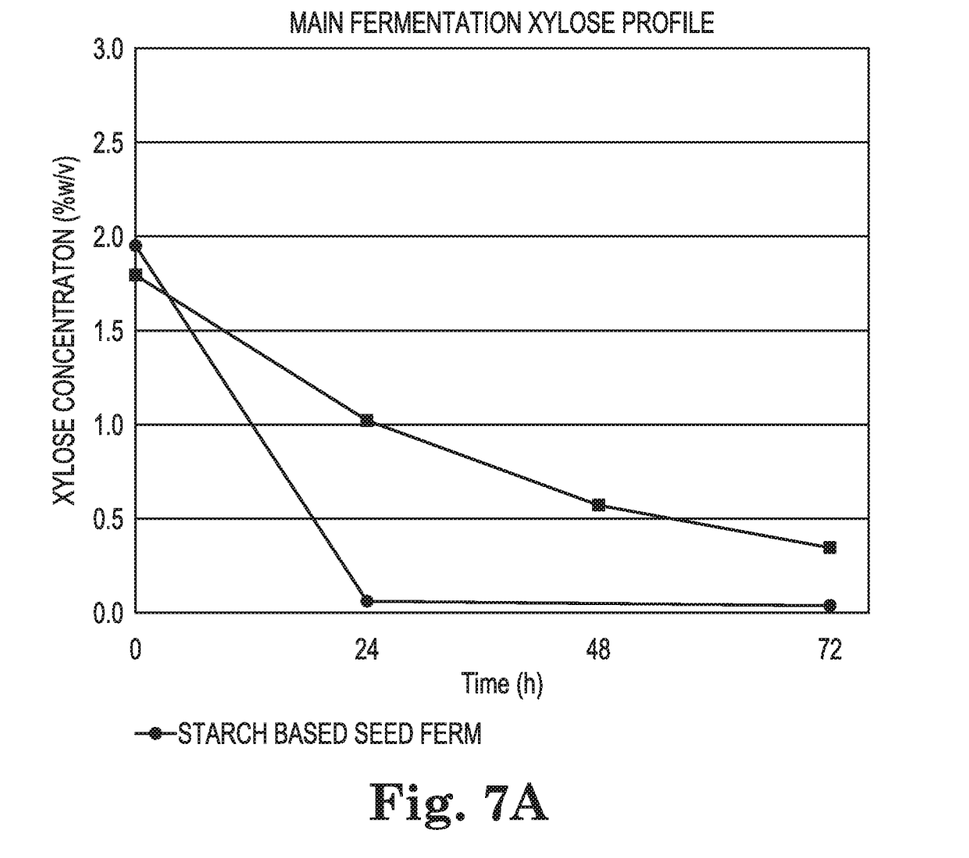
FIG. 7A shows a graph for data in Example 3.
Figure 7B:
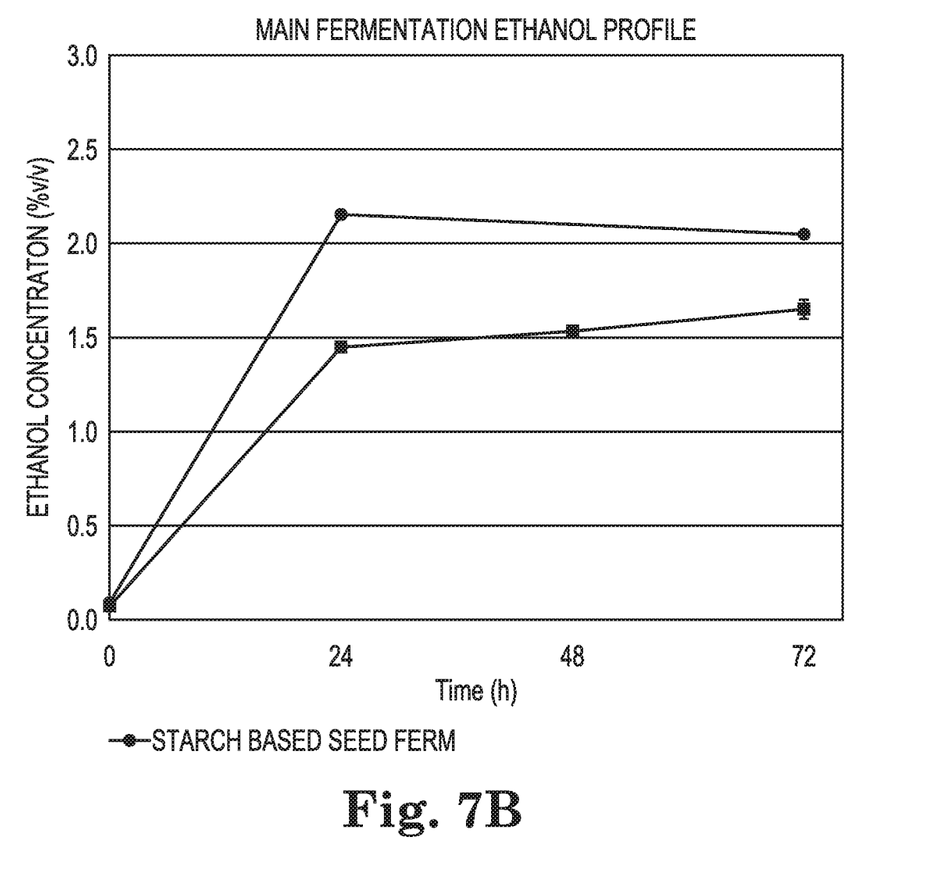
FIG. 7B shows another graph for data in Example 3.
Figure 7C:
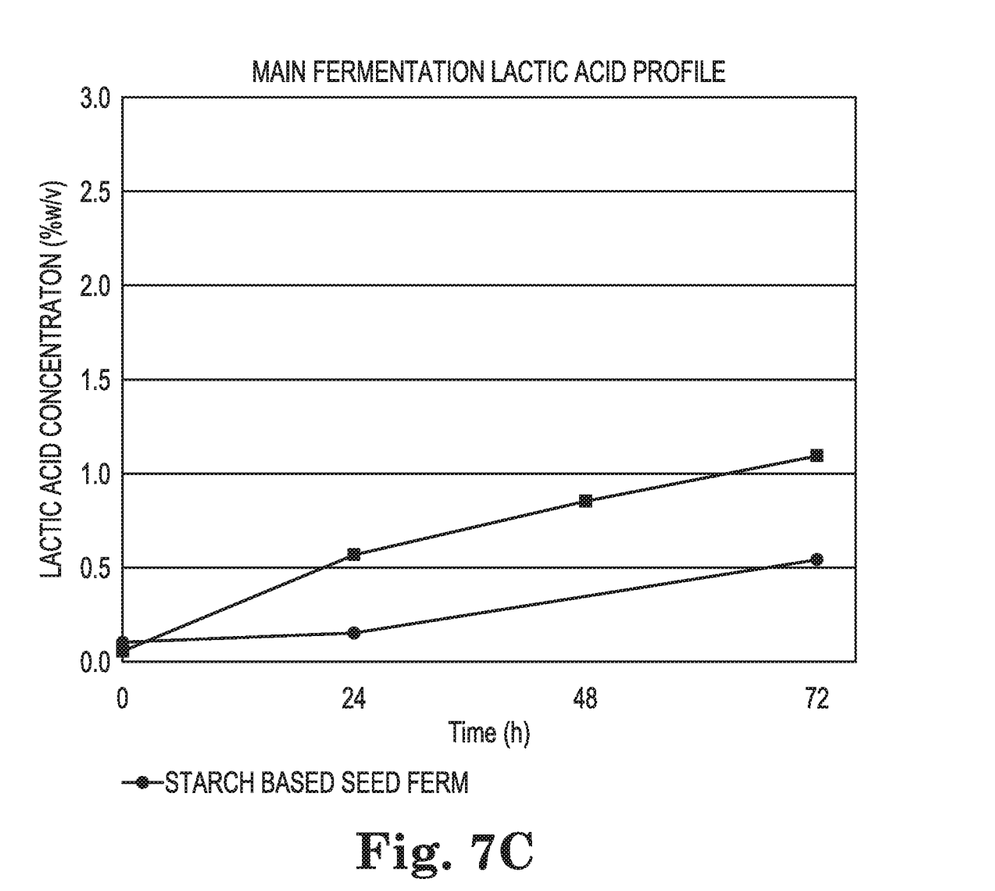
FIG. 7C shows another graph for data in Example 3.

Shown in FIGS. 7A-7C are lab scale main fermentation results using the same fermentation medium comparing the use of propagated cells using starch based propagation media and propagated cells using cellulosic hydrolysate based propagation media. Both propagations used approximately the same total sugar concentration. The results showed that when using propagated cells using starch based propagation media, greater xylose is consumed, greater ethanol is produced, and less lactic acid (from bacterial contamination) is produced. Furthermore, both xylose consumption and ethanol production occur at higher rates.

What is claimed is:

1. A method of propagating a microorganism, the method comprising:
   a) providing a carbon source, wherein the carbon source comprises a ground grain slurry, wherein the ground grain slurry comprises starch;
   b) providing a nutrient source, wherein the nutrient source comprises a grain stillage composition;
   c) providing a source of a first cell mass of a microorganism that can convert a monosaccharide into a biochemical, wherein the microorganism comprises *Saccharomyces cerevisiae* that has been genetically modified to convert xylose and glucose into the biochemical;
   d) providing a source of one or more enzymes than can convert the starch into one or more monosaccharides;
   e) combining the carbon source, the nutrient source, the first cell mass of the microorganism, and the one or more enzymes to form a propagation composition, wherein the propagation composition is exposed to conditions to convert the starch into glucose and propagate the first cell mass of the microorganism into a second cell mass of the microorganism;
   f) providing a lignocellulosic hydrolysate comprising at least glucose, xylose, and furfural; and
   g) combining the lignocellulosic hydrolysate and at least a portion of the second cell mass of microorganism so that the second cell mass of organism can convert the glucose and xylose into a biochemical.

2. The method of claim 1, wherein the one or more enzymes comprise at least one alpha-amylase and at least one gluco-amylase.

3. The method of claim 1, wherein the ground grain slurry comprises ground corn grain.

4. The method of claim 3, wherein the ground corn grain is formed by dry grinding whole corn grain.

5. The method of claim 1, wherein the grain stillage composition comprises thin stillage derived from distilling a corn grain fermentation product.

6. The method of claim 1, wherein the first cell mass of the microorganism is propagated into the second cell mass of the microorganism under aerobic conditions.

7. The method of claim 1, wherein the second cell mass of the microorganism is at least 1000 times greater in number than the first cell mass of the microorganism.

8. The method of claim 1, wherein the first cell mass of the microorganism is $5 \times 10^6$ cells per milliliter of propagation composition or less, and the second cell mass of the microorganism is $1 \times 10^8$ cells per milliliter of propagation composition or more.

9. The method of claim 1, wherein the combining step comprises:
   a) combining the carbon source, the nutrient source, and at least one alpha-amylase to form the propagation composition at a temperature in the range from 65° C. to 80° C., wherein the propagation composition is held a temperature in the range from 65° C. to 80° C. for a time period in the range from 1 to 3 hours, wherein the alpha-amylase facilitates converting at least a portion of the starch to one or more oligosaccharides;
   b) after step (a), cooling the propagation composition to a temperature in the range from 20° C. to 40° C.;
   c) during and/or after step (b), adding gluco-amylase to the propagation composition to facilitate converting the one or more oligosaccharides into glucose; and
   d) after step (b), adding the first cell mass of the microorganism so that the first cell mass of the microorganism can utilize the glucose to propagate into the second cell mass of the microorganism.

10. The method of claim 1, wherein the lignocellulosic hydrolysate further comprises lignin.

11. The method of claim 1, wherein the lignocellulosic hydrolysate is derived from corn stover and corn cobs.

12. The method of claim 1, wherein the propagation medium further comprises cellulosic saccharification broth.

13. The method of claim 1, wherein the conditions in step "e)" comprise aerating the propagation composition.

14. The method of claim 1, wherein the grain stillage composition comprises whole stillage and/or syrup.

15. The method of claim 1, wherein the lignocellulosic hydrolysate is derived from contacting ground corn stover and ground corn cobs with an acid to hydrolyze hemicellulose into one or more pentoses.

16. The method of claim 15, wherein contacting ground corn stover and ground corn cobs with an acid to hydrolyze hemicellulose into one or more pentoses comprises contacting ground corn stover and ground corn cobs with a sulfuric acid composition having a concentration of sulfuric acid in the range from 0.2 to 1.3% w/w.

17. The method of claim 15, wherein contacting ground corn stover and ground corn cobs with an acid to hydrolyze hemicellulose into one or more pentoses is performed at a temperature in the range from greater than 100° C. to 170° C.

18. The method of claim 15, wherein contacting ground corn stover and ground corn cobs with an acid to hydrolyze hemicellulose into one or more pentoses is performed at a temperature in the range from greater than 110° C. to 150° C.

19. The method of claim 15, further comprising, after contacting ground corn stover and ground corn cobs with an acid to hydrolyze hemicellulose into one or more pentoses, contacting ground corn stover and ground corn cobs with one or more cellulase enzymes to hydrolyze cellulose into glucose.

20. The method of claim 19, wherein contacting ground corn stover and ground corn cobs with one or more cellulase enzymes to hydrolyze cellulose into glucose comprises:
   a) liquefying cellulose to form liquefied cellulose; and
   b) saccharifying liquefied cellulose into glucose according to a batch process.

\* \* \* \* \*